United States Patent [19]

Bass et al.

[11] 4,347,239

[45] Aug. 31, 1982

[54] INACTIVATED RABIES VACCINE FOR VETERINARY USE

[75] Inventors: Edmund P. Bass; Richard L. Sharpee, both of Lincoln, Nebr.

[73] Assignee: Norden Laboratories, Inc., Lincoln, Nebr.

[21] Appl. No.: 174,306

[22] Filed: Jul. 30, 1980

[51] Int. Cl.³ ............................................ A61K 39/205
[52] U.S. Cl. ....................................... 424/89; 435/236; 435/237; 435/238
[58] Field of Search ................... 424/89; 435/235–239

[56] References Cited

U.S. PATENT DOCUMENTS

| | | |
|---|---|---|
| 3,397,267 | 8/1968 | Fernandes et al. ................... 424/89 |
| 3,423,505 | 1/1969 | Crawley et al. ...................... 424/89 |
| 3,585,266 | 6/1971 | Emery et al. ......................... 424/89 |
| 3,769,415 | 10/1973 | Fenje ................................... 424/89 |
| 4,040,904 | 8/1977 | Slater ................................... 424/89 |
| 4,070,453 | 1/1978 | Bordet et al. ......................... 424/89 |
| 4,115,195 | 9/1978 | Barth et al. ........................... 424/89 |

FOREIGN PATENT DOCUMENTS

| | | |
|---|---|---|
| 859178 | 1/1978 | Belgium . |
| 863368 | 7/1978 | Belgium . |
| 2162013 | 12/1971 | Fed. Rep. of Germany . |
| 2290220 | 11/1974 | France . |
| 2261779 | 7/1978 | France . |

OTHER PUBLICATIONS

Brown et al., Amer. J. Vet. Res. 28(124):751 (1967).
C. R. Hebd. Seances Acad. Sci. Ser. D. Sci Natur 265(25):2143 (1967).
Crick et al. Res. Vet. Sic 12(2):156 (1971).
Clark, Science 199 (4333):1072 (1978).
Clark, Infect. Immun. 27(3):1012 (1980).
Nawathe et al. Bull. Anim. Health Prod. Afr. 26(1):1 (1978).
Crick et al. Vet. Rec. 99(9):162 (1976).
Plotkin et al. Ann. Rev. Med. 29:583 (1978).
"Compendium of Animal Rabies Vaccines," 1980 J. Amer. Vet Med. Assoc. 176(5):399 (1980).
Bektemirova et al. Arch. Virol 61(1-1): 61 (1979).
McClurkin et al. Can. J. Comp. Med. Vet. Sci. 30:190 (1966).
Chapter 33, Laboratory Techniques in Rabies 3rd edition WHO Geneva (1973).
Chapter 40 Laboratory Techniques in Rabies 3rd edition, WHO Geneva (1973).
Reed and Muench. J. Amer. J. Hygiene 27:493 (1938).

*Primary Examiner*—Shep K. Rose
*Attorney, Agent, or Firm*—Janice E. Williams; Richard D. Foggio; Alan D. Lourie

[57] ABSTRACT

The preparation of a vaccine for immunization of canine and feline animals from inactivated HCP-SAD strain of rabies virus is disclosed.

11 Claims, No Drawings

INACTIVATED RABIES VACCINE FOR VETERINARY USE

This invention relates to veterinary rabies vaccines. More particularly, the invention relates to the propagation of rabies virus in swine testicle cell cultures, to mono- and polyvalent vaccines containing the inactivated rabies virus so propagated and to the use of such vaccines to vaccinate canine and feline animals. The inactivated rabies vaccine of this invention is particularly useful for vaccinating dogs and cats and produces advantageously high antibody responses in cats.

For many years, research has been directed toward the preparation of safe and effective veterinary rabies vaccines [Crick et al., Vet. Rec. 99(9):162 (1976); Plotkin et al., *Ann. Rev. Med.* 29:583 (1978)]. A number of rabies vaccines are currently marketed for use in dogs, cats and other animals. These vaccines are classified as nervous tissue vaccines, avian embryo vaccines and tissue culture vaccines, depending on the medium in which the virus was propagated. The inactivated rabies vaccines currently marketed are of murine (nervous tissue) and hamster cell line origin (tissue culture) [Compendium of Animal Rabies Vaccines, 1980, *J. Amer. Vet. Med. Assoc.* 176(5):399 (1980)] and are known to be of limited safety, particularly in use with cats. In fact, high cell passage SAD rabies strain vaccines are no longer approved by the United States Department of Agriculture for vaccination of cats.

Many known veterinary rabies vaccines comprise virus which has been propagated in tissue culture. For example, the Flury HEP strain was grown in canine kidney cell [Brown et al., *Amer. J. Vet. Res.* 28(124):751 (1967)], the ERA strain was propagated and attenuated in porcine kidney cells (U.S. Pat. No. 3,423,505), the PRI strain was produced by repeated passage of the ERA strain in porcine kidney cells (U.S. Pat. No. 4,040,904) and the ERA strain has been attenuated in bovine kidney cells (U.S. Pat. No. 3,585,266; German Pat. No. 2,162,013). Other cells used for the production of attenuated or inactivated rabies vaccines include hamster fibroblasts [*C. R. Hebd. Seances Acad. Sci. Ser. D. Sci. Natur.* 265(25):2143 (1967)], baby hamster kidney cells [Crick et al., *Res. Vet. Sci.* 12(2):156 (1971); U.S. Pat. No. 3,769,415], chick embryo fibroblasts (U.S. Pat. No. 4,115,195; Belgian Pat. No. 863,368), fetal calf kidney cells (French Pat. Nos. 2,261,779 and 2,290,220), fetal canine lung diploid cells (Belgian Pat. No. 859,178), human diploid cells (U.S. Pat. No. 3,397,267), a diploid porcine embryonic cell strain (U.S. Pat. No. 4,070,453), human and murine neuroblastoma cells [Clark, *Science* 199(4333):1072 (1978) and *Infect. Immun.* 27(3):1012 (1980)], African green monkey kidney cells [Nawathe et al., *Bull. Anim. Health Prod. Afr.* 26(1):1 (1978)] and quail embryo primary cells [Bektemirova et al., *Arch. Virol.* 61(1–2):61 (1979)].

Until the present work, rabies virus has not been adapted for growth in swine testicle cell cultures. The present invention consists of the growth of rabies virus in swine testicle cell cultures, particularly in a diploid swine testicle cell line designated the NL-ST-1 cell line, and the preparation of safe and highly effective mono- and polyvalent vaccines from the inactivated virus for immunization of canine and feline animals against rabies. Swine testicle cell cultures used to propagate the rabies virus are described by McClurkin et al., *Can. J. Comp. Med. Vet. Sci.* 30:190 (1966). Use of the NL-ST-1 cell line for virus production was approved by the United States Department of Agriculture, Animal and Plant Health Inspection Service in November, 1976; a pseudorabies vaccine containing virus propagation on this cell line was licensed and marketed in the United States in 1977.

The monovalent vaccine of this invention is administered parenterally, preferably by intramuscular injection, in one or more doses. Preferably, a single 1.0 ml to 1.2 ml dose of vaccine containing 0.93 ml of inactivated virus-containing fluids having from about $10^{4.0}$ to about $10^{9.0}$ TCID$_{50}$/ml, preferably from about $10^{6.0}$ to about $10^{8.0}$ TCID$_{50}$/ml, combined with a suitable carrier, adjuvant and/or stabilizer is administered. Animals younger than three months of age when initially vaccinated should be revaccinated after reaching the age of three months. Annual revaccination is recommended.

The rabies virus used to prepare the inactivated virus vaccine of this invention is the high cell culture passage of the Street Alabama Dufferin (HCP-SAD) rabies virus strain. This virus was initially isolated from a rabid dog at CDC-Dufferin Laboratories, Montgomery, Alabama in 1935. The isolate was passaged 54 times in mice, followed by 25 passages in hamster kidney cell culture, 10 passages in embryonated chicken eggs and 40 serial passages in porcine kidney cell culture. The virus is then adapted for growth in the swine testicle cell cultures by passaging at least once. The virus may be passaged up to about 25 times in swine testicle cell cultures, with from about 6 to about 12 passages being preferable. Before passaging in swine testicle cells, the virus may be passaged in other mamalian cell cultures such as bovine kidney cell cultures.

After growth in swine testicle cells at from about 34° C. to about 38° C., preferably about 36° C., the virus is inactivated with an inactivating agent which does not destroy the virus particles or antigenicity according to standard methods known to the art. Examples of such inactivating agents are beta-propiolactone or ethyleneimine derivatives, preferably beta-propiolactone.

To prepare the vaccine of this invention, the inactivated rabies virus is combined with an adjuvant, a suitable carrier and/or a stabilizer according to standard, known to the art methods. Any known adjuvant which enhances the antigenicity of the vaccine, for example aluminum hydroxide gel, may be used.

It has been found that a single 1.0 ml intramuscular vaccination with the inactivated rabies vaccine of this invention having a titer of about $10^{6.0}$ to about $10^{8.0}$ TCID$_{50}$/ml elicited significant serological responses in 100% of vaccinated dogs. At one year following vaccination, 96% of these dogs remained protected against challenge with virulent virus which killed 100% of the unvaccinated controls. In cats, vaccination with a single 1.0 ml intramuscular vaccination of the inactivated rabies vaccine of this invention having a titer of about $10^{6.0}$ to about $10^{8.0}$ TCID$_{50}$/ml produced a surprising and highly significant serological response in 100% of the vaccinated animals. At one year following vaccination, 100% of these cats remained protected against challenge with virulent virus which killed 90% of the unvaccinated controls. Thus, the inactivated rabies vaccine of the present invention is a safe and effective veterinary vaccine, being particularly safe, effective and superior to prior art vaccines for protecting felines against rabies.

The inactivated rabies vaccine of this invention has been licensed for use in dogs and cats by the United States Department of Agriculture, Animal and Plant Health Inspection Services on June 16, 1980. It is believed to be the only vaccine containing the SAD strain of rabies virus approved for use in cats.

DETAILED DESCRIPTION OF THE INVENTION

Preparation of the Inactivated Rabies Vaccine

The high cell passage of Street Alabama Dufferin (HCP-SAD) strain of rabies virus was used to prepare the inactivated rabies vaccine of this invention. This virus was obtained from a commercial rabies vaccine manufactured by Jensen-Salsbury Laboratories, Kansas City, Missouri at the 129th passage level and was further transferred for 15 additional serial passages in a bovine kidney cell culture and 6 serial passages in the swine testicle cell line, NL-ST-1. The 150th passage was designated as the master seed virus. The virus was identified by specific immunofluorescence of infected cell cultures stained with fluorescein conjugated rabies specific antiserum. Viral antigen was demonstrated in the cytoplasm of infected cells. The virus was also identified by neutralization with specific rabies antiserum. Virulence was demonstrated by intracerebral inoculation of the master seed virus into young adult mice.

For propagation of the master seed virus, frozen ampoules of NL-ST-1 cells were thawed and reconstituted to sufficient volume for seeding in production flasks. The production flasks were allowed to incubate at 36° C. until a confluent cell monolayer formed (3 to 5 days). Passage of these cells was accomplished by use of a combination of versene-trypsin and the cells were expanded in volume to plant sufficient numbers in production flasks for inoculation. While the cells were suspended in the growth medium, master seed virus fluids were added to the suspension at 0.1% of total medium volume. Production flasks were planted with the virus-inoculated growth medium and the cells allowed to multiply until 90–100% confluency of cell monolayer was achieved (3 to 5 days). These virus-infected cells were removed from the production flasks with versene-trypsin and suspended in maintenance medium. Production flasks were planted with maintenance medium containing the virus-infected cell suspension and maintained at 36° C. until harvest. Replication of the rabies virus is complete at the time of appearance of cytopathogenic effects, characterized by rounded cells which subsequently become detached from the cell monolayers. Contamination was detected by gross and microscopic examination. Titer of the master seed virus inoculum was at least $10^{6.0}$ $TCID_{50}$/ml.

Harvest of virus-laden fluids following production flask planting, which is dependent upon the cytopathogenic changes occurring in the infected monolayer, occured after 3 to 6 days. The virus-laden fluid was transferred and pooled into sterile storage containers under sterile environmental conditions. Samples of harvested fluids were tested for sterility and virus titer. Only fluids found to be pure were used for vaccine preparation. Virus titer of the harvested fluids must be from about $10^{4.0}$ to about $10^{9.0}$ $TCID_{50}$/ml.

To inactivate the harvested virus, beta-propiolactone was added to the pooled fluids at pH 6.8 to 7.4 to a final concentration of 1:6000 (0.017%). The virus containing fluids were maintained at 4° C. with constant stirring for 48 hours. Following inactivation, merthiolate (thimersol, N.F.) was added as a preservative to give a final concentration of 1:10,000. After the addition of merthiolate, the product was stored at 4° C. until addition of adjuvant.

The inactivated virus fluids were pooled, the pH was adjusted to 6.0 with 4 N HCl and aluminum hydroxide gel (2% $Al_2O_3$) was added as adjuvant until a final concentration of 5% by volume. The inactivated virus-aluminum hydroxide gel mixture was stirred for 2 hours at 4° C. The vaccine thus prepared was tested for safety and potency and stored at 4° C.

An accelerated stability study was conducted to determine stability of the vaccine. After incubation of samples of a vaccine prepared as described above at 37° C. for one week, there was a loss of 0.04 relative potency as compared with a sample stored at 4° C.

The relative potency of the vaccine was determined by the National Institutes of Health (NIH) mouse potency test described in Chapter 33 of "Laboratory Techniques in Rabies", 3rd edition, WHO, Geneva (1973) by comparing test results of five samples of the vaccine to test results of five samples of NIH standard reference vaccine. The geometric mean relative potency value was 0.15.

Use of the Inactivated Rabies Vaccine

The inactivated rabies virus vaccine was used to vaccinate susceptible dogs and cats. Rabies-susceptible dogs were obtained from commercial sources and ranged in age from 4.5 to 7.5 months when vaccinated. Rabies-susceptible cats were obtained from commercial sources and ranged in age from 7 to 13 months when vaccinated. Each animal was vaccinated intramuscularly at one site in the thigh with a single 1 ml dose of vaccine having a titer of $10^{6.4}$ $TCID_{50}$/ml, either undiluted (full dose) or diluted 1:2 (half dose). The half dose vaccine was prepared by mixing equal amounts of the undiluted vaccine and diluent containing 5% aluminum hydroxide gel. All vaccinated animals were bled prior to vaccination and at 30, 60, 90, 180, 270 and 365 days following vaccination. Serum was collected and evaluated for the presence of serum neutralizing rabies antibody in accordance with the Quantitative Assay and Potency Test of Antirabies Serum and Immunoglobulin in Chapter 40 of "Laboratory Techniques in Rabies", 3rd edition, WHO, Geneva (1973). Serum-neutralization (SN) antibody titer was determined by the method of Reed and Muench, *J. Amer. J. Hygiene* 27:493 (1938).

At 365 days following vaccination, the immunity of the test animals was challenged with virulent NYC strain of street rabies virus. The challenge virus was a dilution of a 20% fox brain suspension.

Vaccination and Challenge of Dogs

Twenty-six dogs determined to be serologically negative to rabies virus were vaccinated with a full dose of the inactivated rabies vaccine. At 30 days following vaccination, the sera of the vaccinates contained a geometric mean antibody titer of 1:109, with titers ranging from 1:32 to 1:431. During a one year serological evaluation, titers gradually declined to a geometric mean antibody titer of 1:10 at 365 days following vaccination. Twenty susceptible control dogs were inoculated with virulent NYC strain of street rabies virus, ten animals receiving virus diluted 1:150 and ten receiving virus diluted 1:300. One year (365 days) following vaccination, the vaccinated dogs were challenged with a 1:150 dilution of the virulent rabies virus (NYC strain of street rabies virus). Twenty-five out of twenty-six (96%) of the vaccinates remained normal throughout the 90 day period following challenge. The results from this test appear in Table 1; results from the control animals appear in Table 3.

Twenty-five dogs determined to be serologically negative to rabies virus were vaccinated with a half dose (1:2) of the inactivated rabies vaccine. At 30 days following vaccination, the sera of the vaccinates contained a geometric mean antibody titer of 1:42, with titers ranging from 1:8 to 1:204. Titers gradually declined to a geometric mean antibody titer of 1:7 at 365 days following vaccination. The immunity of the animals was challenged with virulent NYC strain of street rabies virus 365 days following vaccination. Twenty-three out of twenty-five (92%) of the vaccinated dogs survived challenge. The results from this test appear in Table 2; results from the control animals appear in Table 3.

Vaccination and Challenge of Cats

Twenty-five cats determined to be serologically negative to rabies virus were vaccinated with a full dose of the inactivated rabies vaccine. At 30 days following vaccination, the sera of the vaccinates contained a geometric mean antibody titer of 1:1328, with titers ranging from 1:214 to 1:8192. At 365 days following vaccination, the geometric mean antibody titer was 1:88 with titers ranging from 1:26 to 1:1024. As controls, twenty susceptible cats were inoculated with virulent NYC strain of street rabies virus, ten animals receiving virus diluted 1:30 and ten receiving virus diluted 1:60. The immunity of the vaccinated cats was challenged at 365 days following vaccination with virulent rabies virus (NYC strain of street rabies virus). All (100%) of the vaccinated cats remained normal throughout the 90 day period following challenge. The results from this test appear in Table 4; results from the control animals appear in Table 5.

TABLE 1

Protection Afforded Dogs by Vaccination with Inactivated Rabies Vaccine, Swine Testicle Cell Line Origin (Full Dose)

| Dog No. | Serum Neutralization Titer* Following Vac. (days) | | | | | | Status Post Challenge |
|---|---|---|---|---|---|---|---|
| | 0 | 30 | 60 | 90 | 180 | 270 | 365 | |

| Dog No. | 0 | 30 | 60 | 90 | 180 | 270 | 365 | Status Post Challenge |
|---|---|---|---|---|---|---|---|---|
| 10 | Neg. | 81 | 16 | 8 | 4 | 13 | 64 | Normal |
| 11 | Neg. | 38 | 5 | 4 | 3 | Neg. | Neg. | Normal |
| 16 | Neg. | 38 | 41 | 13 | 5 | 2 | 2 | Normal |
| 20 | Neg. | 206 | 19 | 8 | 3 | 5 | 10 | Normal |
| 22 | Neg. | 128 | 10 | 4 | 3 | 4 | 13 | Died (Rabies, Day 19) |
| 23 | Neg. | 128 | 54 | 64 | 19 | 19 | 2 | Normal |
| 27 | Neg. | 64 | 76 | 81 | 54 | 64 | 51 | Normal |
| 29 | Neg. | 203 | 41 | 19 | 25 | 32 | 38 | Normal |
| 31 | Neg. | 203 | 41 | 65 | 54 | 25 | 32 | Normal |
| 45 | Neg. | 431 | 12 | 11 | 13 | 5 | 5 | Normal |
| 62 | Neg. | 128 | 5 | 4 | 6 | 2 | 4 | Normal |
| 79 | Neg. | 98 | 5 | 8 | 13 | 25 | 16 | Normal |
| 82 | Neg. | 87 | 214 | 54 | 13 | 11 | 10 | Normal |
| 83 | Neg. | 431 | 13 | 64 | 76 | 64 | 128 | Normal |
| 94 | Neg. | 182 | 19 | 19 | 19 | 19 | 54 | Normal |
| 97 | Neg. | 203 | 25 | 21 | 19 | 13 | 6 | Normal |
| 98 | Neg. | 38 | 16 | 64 | 16 | 6 | 3 | Normal |
| 99 | Neg. | 203 | 54 | 16 | 16 | 10 | 6 | Normal |
| 100 | Neg. | 32 | 5 | 54 | 25 | 13 | 13 | Normal |
| 101 | Neg. | 256 | 19 | 54 | 19 | 16 | 10 | Normal |
| 107 | Neg. | 81 | 3 | 3 | 4 | 4 | 10 | Normal |
| 112 | Neg. | 38 | 10 | 54 | 6 | 4 | 2 | Normal |
| 144 | Neg. | 81 | 128 | 46 | 13 | 10 | 19 | Normal |
| 145 | Neg. | 107 | 20 | 16 | 6 | 16 | 10 | Normal |
| 154 | Neg. | 81 | 41 | 6 | 2 | Neg. | 2 | Normal |
| 155 | Neg. | 85 | 32 | 19 | 2 | 3 | 2 | Normal |
| Geo. Mean | Neg. | 109 | 21 | 19 | 10 | 10 | 10 | |

TABLE 1-continued

Protection Afforded Dogs by Vaccination with Inactivated Rabies Vaccine, Swine Testicle Cell Line Origin (Full Dose)

*Titer expressed as reciprocal of serum-neutralization end point.

TABLE 2

Protection Afforded Dogs by Vaccination with Inactivated Rabies Vaccine, Swine Testicle Cell Line Origin (Half Dose)

| Dog No. | 0 | 30 | 60 | 90 | 180 | 270 | 365 | Status Post-Challenge |
|---|---|---|---|---|---|---|---|---|
| 2 | Neg. | 8 | 3 | 5 | 5 | 3 | 2 | Normal |
| 3 | Neg. | 20 | 4 | 2 | 4 | 5 | 3 | Normal |
| 4 | Neg. | 204 | 54 | 25 | 13 | 6 | 16 | Normal |
| 19 | Neg. | 20 | 5 | 5 | 4 | 5 | 3 | Normal |
| 21 | Neg. | 81 | 5 | 10 | 4 | 4 | 3 | Normal |
| 42 | Neg. | 51 | 41 | 10 | 3 | 2 | Neg. | Normal |
| 43 | Neg. | 151 | 46 | 25 | 5 | 4 | 3 | Normal |
| 64 | Neg. | 32 | 5 | 14 | 8 | 13 | 4 | Normal |
| 67 | Neg. | 27 | Neg. | 2 | 5 | 3 | Neg. | Normal |
| 74 | Neg. | 32 | 6 | 3 | Neg. | 6 | 3 | Normal |
| 78 | Neg. | 16 | 2 | 2 | 2 | 2 | 4 | Normal |
| 81 | Neg. | 32 | 3 | 3 | 13 | 6 | 10 | Normal |
| 103 | Neg. | 13 | 4 | 3 | 4 | 3 | 4 | Normal |
| 104 | Neg. | 13 | 22 | 10 | Neg. | 3 | 2 | Died (Rabies, day 14) |
| 108 | Neg. | 51 | 13 | 6 | 13 | 10 | 32 | Normal |
| 109 | Neg. | 51 | 11 | 8 | 4 | 4 | 5 | Normal |
| 110 | Neg. | 32 | 5 | 5 | 3 | 3 | 4 | Normal |
| 111 | Neg. | 28 | 4 | 2 | 3 | Neg. | Neg. | Normal |
| 115 | Neg. | 38 | 10 | 3 | 8 | 6 | 6 | Died (Rabies, day 14) |
| 118 | Neg. | 166 | 32 | 41 | 13 | 20 | 21 | Normal |
| 123 | Neg. | 81 | 41 | 25 | 25 | 11 | 54 | Normal |
| 125 | Neg. | 81 | 13 | 3 | Neg. | 4 | Neg. | Normal |
| 126 | Neg. | 27 | 13 | 16 | 13 | 10 | 13 | Normal |
| 143 | Neg. | 128 | 19 | 19 | 16 | 20 | 19 | Normal |
| 147 | Neg. | 151 | 16 | 41 | 41 | 102 | 54 | Normal |
| Geo. Mean | Neg. | 42 | 10 | 7 | 7 | 6 | 7 | |

*Titer expressed as reciprocal of serum-neutralization end point.

TABLE 3

Dog Controls - 20% Fox Brain Suspension of NYC Strain of Street Rabies Virus (0.5 ml Bilateral Masseter Muscles)

| Challenge Dilution | Dog. No. | Observations |
|---|---|---|
| 1:150 | 70 | Rabies - Day 11 |
| | 71 | Rabies - Day 10 |
| | 87 | Rabies - Day 10 |
| | 106 | Rabies - Day 10 |
| | 116 | Rabies - Day 10 |
| | 130 | Rabies - Day 13 |
| | 132 | Rabies - Day 12 |
| | 135 | Rabies - Day 13 |
| | 136 | Rabies - Day 10 |
| | 137 | Rabies - Day 14 |
| 1:300 | 1 | Rabies - Day 13 |
| | 5 | Rabies - Day 13 |
| | 9 | Rabies - Day 12 |
| | 49 | Rabies - Day 13 |
| | 86 | Rabies - Day 11 |
| | 91 | Rabies - Day 10 |
| | 105 | Survived |
| | 124 | Rabies - Day 13 |
| | 134 | Rabies - Day 11 |
| | 150 | Rabies - Day 10 |

TABLE 4

Protection Afforded Cats by Vaccination with Inactivated Rabies Vaccine, Swine Testicle Cell Line Origin (Full Dose)

| Cat No. | Serum Neutralization Titer* Following Vac. (days) | | | | | | | Status Post-Challenge |
|---|---|---|---|---|---|---|---|---|
| | 0 | 30 | 60 | 90 | 180 | 270 | 365 | |
| NA6 | Neg. | 6166 | 64 | 102 | 64 | 100 | 64 | Normal |
| NF3 | Neg. | 407 | 646 | 407 | 151 | 263 | 64 | Normal |
| WK1 | Neg. | 8192 | 102 | 151 | 128 | 407 | 101 | Normal |
| WQ3 | Neg. | 2028 | 64 | 32 | 32 | 64 | 64 | Normal |
| SA2 | Neg. | 302 | 64 | 23 | 32 | 42 | 40 | Normal |
| WV4 | Neg. | 304 | 64 | 41 | 20 | 51 | 64 | Normal |
| NC1 | Neg. | 5248 | 256 | 128 | 324 | 214 | 64 | Normal |
| OG4 | Neg. | 1024 | 64 | 32 | 64 | 64 | 50 | Normal |
| NA1 | Neg. | 512 | 1024 | 1230 | 603 | 1622 | 256 | Normal |
| XB2 | Neg. | 1622 | 64 | 64 | 51 | 51 | 64 | Normal |
| SB3 | Neg. | 1024 | 64 | 91 | 128 | 214 | 64 | Normal |
| WD2 | Neg. | 1445 | 302 | 813 | 603 | 817 | 215 | Normal |
| NF4 | Neg. | 1660 | 76 | 64 | 128 | 54 | 54 | Normal |
| NA3 | Neg. | 8192 | 302 | 813 | 151 | 76 | 64 | Normal |
| NC4 | Neg. | 407 | 64 | 54 | 128 | 162 | 54 | Normal |
| BA1 | Neg. | 6457 | 302 | 128 | 151 | 407 | 215 | Normal |
| LD3 | Neg. | 256 | 56 | 32 | 46 | 32 | 16 | Normal |
| SB1 | Neg. | 8192 | 1622 | 1122 | 1738 | 1445 | 406 | Normal |
| SC3 | Neg. | 1318 | 102 | 162 | 151 | 427 | 101 | Normal |
| SA1 | Neg. | 512 | 64 | 16 | 64 | 107 | 64 | Normal |
| LC3 | Neg. | 407 | 64 | 81 | 107 | 128 | 40 | Normal |
| SG5 | Neg. | 4096 | 646 | 512 | 1230 | 1024 | 1024 | Normal |
| BC1 | Neg. | 214 | 102 | 151 | 427 | 646 | 304 | Normal |
| OF1 | Neg. | 407 | 54 | 38 | 64 | 256 | 64 | Normal |
| BB2 | Neg. | 6456 | 214 | 43 | 50 | 51 | 64 | Normal |
| Geo. Mean | Neg. | 1328 | 138 | 112 | 130 | 178 | 88 | |

*Titer expressed as reciprocal of serum-neutralization end point.

TABLE 5

Cat Controls - 20% Fox Brain Suspension of NYC Strain Street Rabies Virus (0.25 ml Bilateral Neck Muscles)

| Challenge Dilution | Cat No. | Observations |
|---|---|---|
| 1:30 | 22 | Rabies - Day 15 |
| | 23 | Rabies - Day 20 |
| | 24 | Rabies - Day 14 |
| | WQ2 | Rabies - Day 13 |
| | WL1 | Survived |
| | 25 | Rabies - Day 20 |
| | 26 | Rabies - Day 29 |
| | 28 | Rabies - Day 35 |
| | OF6 | Rabies - Day 57 |
| | SC2 | Rabies - Day 29 |
| 1:60 | ND1 | Survived |
| | ND2 | Rabies - Day 12 |
| | NC3 | Rabies - Day 31 |
| | NA4 | Survived |
| | NF2 | Rabies - Day 17 |
| | BF2 | Rabies - Day 11 |
| | BA3 | Rabies - Day 34 |
| | WS3 | Rabies - Day 36 |
| | OG2 | Rabies - Day 13 |
| | OF3 | Rabies - Day 36 |

A further aspect of this invention is the preparation and use of combination polyvalent vaccines comprising vaccinal amounts of the adjuvanted inactivated rabies virus described herein and one or more canine or feline viruses. For example, feline vaccines comprising vaccinal amounts of modified feline rhinotracheitis virus, calicivirus, and/or panleukopenia virus combined with the inactivated rabies virus can be prepared. Such polyvalent vaccine will, preferably, contain from about 30% to about 70% total volume of the inactivated rabies virus, depending on the number of viruses in combination. An example of such a polyvalent feline vaccine contemplated by this invention comprises about 40% of the inactivated rabies virus, about 20% of feline rhinotracheitis virus, about 20% of calicivirus and about 20% of panleukopenia virus (all percentages based on total volume).

Likewise, canine vaccines comprising vaccinal amounts of distemper virus, canine adenovirus type 2 and para-influenza virus combined with the inactivated rabies virus can be prepared. Leptospira bacterin may also be added to such polyvalent vaccine. The polyvalent vaccine will, preferably, contain from about 30% to about 40% total volume of the inactivated rabies virus. An example of a polyvalent canine vaccine contemplated by this invention comprises about 40% of the inactivated rabies virus, about 40% of distemper virus and about 20% total of all other micro-organisms in the combination (all percentages based on total volume).

The polyvalent vaccines of this invention are administered parenterally, preferably by intramuscular injection.

What is claimed is:

1. An inactivated rabies virus vaccine capable of inducing immunity in feline animals without serious side effects comprising a vaccinal amount of inactivated HCP-SAD strain of rabies virus which has been adapted, before inactivation, to grow in swine testicle cell cultures, an adjuvant and a carrier therefor.

2. The inactivated rabies vaccine of claim 1 wherein the rabies virus is passaged at least once in a swine testicle cell culture.

3. The inactivated rabies vaccine of claim 2 wherein the rabies virus is passaged from 1 to about 25 times in a swine testicle cell culture.

4. The inactivated rabies vaccine of claim 3 wherein the rabies virus is passaged from about 6 to about 12 times in a swine testicle cell culture.

5. The inactivated rabies vaccine of claim 1, 2, 3 or 4 wherein the swine testicle cell culture is the NL-ST-1 swine testicle cell line.

6. The inactivated rabies vaccine of claim 5 wherein the virus is inactivated with beta-propiolactone.

7. The inactivated rabies vaccine of claim 5 wherein the adjuvant is aluminum hydroxide gel.

8. A method of vaccinating feline animals comprising administering parenterally to said animals the inactivated rabies vaccine of claim 1, 2, 3 or 4.

9. A method of vaccinating feline animals comprising administering parenterally to said animals the inactivated rabies vaccine of claim 5.

10. The method of claim 8 wherein the vaccine is administered by intramuscular injection.

11. The method of claim 9 wherein the vaccine is administered by intramuscular injection.

* * * * *